US009675432B2

(12) United States Patent
Lee et al.

(10) Patent No.: US 9,675,432 B2
(45) Date of Patent: Jun. 13, 2017

(54) METHOD AND APPARATUS FOR PREPARING REMOVABLE DENTAL PROSTHESIS

(71) Applicant: DENTCA, Inc., Torrance, CA (US)

(72) Inventors: Jae Sik Lee, Los Angeles, CA (US); Tae Hyung Kim, La Canada, CA (US); Sun Kwon, Arcadia, CA (US)

(73) Assignee: DENTCA, Inc., Torrance, CA (US)

( * ) Notice: Subject to any disclaimer, the term of this patent is extended or adjusted under 35 U.S.C. 154(b) by 199 days.

(21) Appl. No.: 14/313,918

(22) Filed: Jun. 24, 2014

(65) Prior Publication Data

US 2014/0308624 A1    Oct. 16, 2014

Related U.S. Application Data

(63) Continuation-in-part of application No. 13/598,413, filed on Aug. 29, 2012, now Pat. No. 8,899,983.
(Continued)

(51) Int. Cl.
*A61C 13/00* (2006.01)
*A61C 9/00* (2006.01)
*A61C 19/05* (2006.01)

(52) U.S. Cl.
CPC ........ *A61C 13/0004* (2013.01); *A61C 9/0006* (2013.01); *A61C 13/0019* (2013.01); *A61C 19/05* (2013.01)

(58) Field of Classification Search
CPC .................... A61C 13/0013; A61C 13/0019
See application file for complete search history.

(56) References Cited

U.S. PATENT DOCUMENTS 310,407 A    1/1885  Gamer
3,626,594 A  12/1971 Zinner et al.
(Continued)

FOREIGN PATENT DOCUMENTS

JP    33-17491    10/1958
JP    11-318953   11/1999
(Continued)

OTHER PUBLICATIONS

Japan Patent Office Application Serial No. 2012-511977, Office Action dated Feb. 6, 2014, 6 pages.
(Continued)

*Primary Examiner* — Michael Kahelin
(74) *Attorney, Agent, or Firm* — Lee, Hong, Degerman, Kang & Waimey

(57) ABSTRACT

A method for manufacturing a removable dental prosthesis using a three-dimensional (3D) printer includes receiving dental impressions of a patient obtained using a dental impression tray assembly, the dental impressions including a bite registration and at least a mandibular impression or a maxillary impression; receiving information related to the patient's jaw relations obtained using the dental impression tray assembly, the jaw relations including a vertical dimension and a centric relation obtained during the patient's single visit to a dentist; scanning the received dental impressions with a 3D scanner to provide data representative of an edentulous shape of the patient; generating a 3D model of the dental prosthesis based on the data and the received information related to the patient's jaw relations using 3D design software; displaying the generated 3D model on a display, allowing customization of the 3D model; and 3D printing the dental prosthesis according to the 3D model.

21 Claims, 4 Drawing Sheets

Related U.S. Application Data which is a continuation of application No. 12/782,663, filed on May 18, 2010, now Pat. No. 8,277,216.

(60) Provisional application No. 61/870,100, filed on Aug. 26, 2013, provisional application No. 61/179,698, filed on May 19, 2009.

(56) References Cited

U.S. PATENT DOCUMENTS

| | | | |
|---|---|---|---|
| 3,890,711 | A | 6/1975 | Burns |
| 4,145,812 | A | 3/1979 | Johnson et al. |
| 4,543,062 | A | 9/1985 | Lee |
| 4,657,509 | A | 4/1987 | Morris |
| 4,789,334 | A | 12/1988 | Wedenig et al. |
| 5,186,624 | A | 2/1993 | Gottsleben |
| 5,722,828 | A | 3/1998 | Halstrom |
| 6,079,981 | A * | 6/2000 | Sekendur ........... A61C 13/0001 433/171 |
| 6,196,840 | B1 | 3/2001 | Zentz et al. |
| 6,231,339 | B1 | 5/2001 | Skarky |
| 8,070,489 | B2 | 12/2011 | Massad |
| 8,277,216 | B2 | 10/2012 | Kim |
| 8,899,983 | B2 | 12/2014 | Kim |
| 2003/0180681 | A1 | 9/2003 | Kwon et al. |
| 2007/0190492 | A1 | 8/2007 | Schmitt |
| 2008/0254406 | A1 | 10/2008 | Wagner |
| 2009/0117514 | A1 * | 5/2009 | Massad ............. A61C 9/0006 433/39 |
| 2009/0287332 | A1 * | 11/2009 | Adusumilli ........ A61C 13/0004 700/98 |

FOREIGN PATENT DOCUMENTS

| | | |
|---|---|---|
| JP | 2006-192223 | 7/2006 |
| JP | 2009-517144 | 4/2009 |
| KR | 10-2009-0036643 | 4/2009 |
| WO | 02-00134 | 1/2002 |
| WO | 2008/083857 | 7/2008 |

OTHER PUBLICATIONS

The State Intellectual Property Office of the People's Republic of China Application Serial No. 201080021927.3, Office Action dated Jan. 21, 2014 7 pages.

United States Patent and Trademark Office U.S. Appl. No. 12/782,663, Advisory Action dated Jun. 6, 2012, 3 pages.

* cited by examiner (a)  (b)

METHOD AND APPARATUS FOR PREPARING REMOVABLE DENTAL PROSTHESIS

CROSS REFERENCE TO RELATED APPLICATIONS

Pursuant to 35 U.S.C. §119(e), this application claims the benefit of U.S. Provisional Application No. 61/870,100, filed on Aug. 26, 2013 and this is a continuation-in-part of U.S. patent application Ser. No. 13/598,413, filed on Aug. 29, 2012, now U.S. Pat. No. 8,899,983, which is a continuation of U.S. patent application Ser. No. 12/782,663, filed on May 18, 2010, now U.S. Pat. No. 8,277,216, which pursuant to 35 U.S.C. §119(e) claims the benefit of U.S. Provisional Application No. 61/179,698, filed on May 19, 2009, the contents of which are all hereby incorporated by reference herein in their entirety.

FIELD OF THE INVENTION

The present disclosure relates generally to preparation of a removable dental prosthesis. In particular, the present invention is directed to a system, an apparatus, and a method for fabricating a denture using a three-dimensional (3D) printing technology. The present invention employs a dental impression tray that allows obtaining an impression of a patient in a single visit by the patient, thus significantly decreasing time required to fabricate the denture. The present invention further employs design software to create an accurate 3D denture model by incorporating all information obtained from a patient in a relatively short period of time. In addition, the present invention employs application software and try-in to allow dentists or technicians to modify and generate a more customized denture model and a 3D printing method to fabricate the denture.

DESCRIPTION OF THE RELATED ART

Dentures are conventionally constructed and fitted by dentists with the assistance of dental technicians using a flask investment technique. This complex process requires measurements of masticatory function, impressions of the gum and surrounding tissues of the affected area, study models and working models, and a series of back and forth steps between the dentist and the dental technician to manufacture the denture. The entire process of constructing dentures using conventional methods and devices requires a number of appointments between the dentist and the patient, and involves a significant amount of time and skill.

Generally, a patient must make a plurality of visits to a dentist to make a set of dentures. Such visits are necessary in order for a dentist to take an impression of the patient's gums, as well as a bite registration of the patient's jaw position and vertical dimension. Information collected during the conventional multiple patient visit procedure includes finding an accurate shape of edentulous ridges, bite registration of the patient's jaw position and vertical dimension, ideal teeth set-up for the patient, and necessary adjustments regarding fit and occlusion.

For example, during a first visit, a dentist examines a patient and takes a preliminary impression of the patient using stock impression trays. After the preliminary impression is taken on the impression material, the impression tray is delivered to a laboratory. In the laboratory, plaster is poured onto the preliminary impression to form accurate models of the shape of the edentulous ridges. The preliminary impression is used to make custom fitting impression trays for a final impression.

During a second visit, the dentist checks and adjusts the custom fitting impression trays as necessary and takes the final impression. Afterwards, in the laboratory, a master model is created and a base plate is fabricated based on the final impression received from the dentist. Then, a bite registration rim or block, usually made of wax, is fabricated from the master gum mold. The master gum mold, with the bite registration rim attached thereto, is sent back to the dentist.

During a third visit, the bite registration rim is inserted into the mouth of the patient, and adjusted inside the mouth to determine maxilla-mandibular relations and to take a bite registration. Further, artificial teeth to be used for the denture are selected by the dentist and the patient by determining a gum shade, teeth size, and teeth shade. The adjusted bite registration rim is sent back to the laboratory to fabricate a wax try-in. The laboratory returns the wax try-in with the actual final teeth lined up along the outer edge of the wax rim. The wax try-in looks similar to a real denture except that the base fits loosely on the gums and the teeth are embedded in wax instead of plastic.

During a fourth visit, the dentist examines how the wax try-in looks and works in the patient, checking occlusal and vertical dimension, necessary adjustments of the try-in being made as necessary. If adjustments are necessary, the wax try-in can be sent back to the laboratory to reset the teeth. If no adjustments are needed, the wax try-in is sent back to the laboratory to be processed and finished. In the laboratory, the wax try-in is converted to a final denture using plastic molding.

During a fifth visit, the final denture is inserted into the mouth of the patient and adjusted as needed. The final denture is also checked for occlusion and corrected as necessary. Occlusion means simply the contact between teeth. More technically, it is the relationship between the maxillary (upper) and mandibular (lower) teeth when they approach each other, as occurs during chewing or at rest. As discussed above, it may generally take at least four or more visits of a patient until the finished dentures are finally inserted into the mouth of the patient. Thus, the multi-step process of preparing a set of dentures, requiring several iterations between the dentist and the dental laboratory is time-consuming, labor intensive and costly.

Moreover, difficulties exist in producing a good quality denture due to the great diversity in sizes and shapes of patients' mouths, and facial features requiring custom fabrication of each denture. Thus, standardization of prefabricated dentures is very difficult. Proposals to overcome the shortcomings of the conventional methods, such as multiple visits, intensive labor, and laboratory time needed for the fabrication of dentures, have had little success.

Therefore, it is critical to get all the necessary information involving the patient mouth on the first visit in order to reduce the number of total visits, and to generate final dentures without compromising quality. Conventional impression trays have difficulties capturing the jaw relation because the tray must be inserted in the patient mouth in order to measure the jaw relation, and the end portions of the upper and lower trays contact each other at the posterior position of the mouth to create interference due to their sizes. Alternatively, jaw relations are measured using other tools and by taking another impression from the first visit.

In the conventional method, the impression was duplicated using a wax after preparing stone cast which requires lengthy time and intensive labor work. Further, in the conventional method, a jaw relation was measured using a wax try-in such that an additional visit of the patient is required.

Recently, three-dimensional (3D) scanners have been developed to record a shape of an object digitally. The 3D scanners are extensively used in industrial design, prosthetics and orthotics, rapid prototyping, and quality control. For example, U.S. Pat. No. 5,266,030 describes using a 3D scanner in dentistry. In particular, U.S. Pat. No. 5,266,030 discloses that scanned teeth data are used to recognize and establish a location of preparation line of part of teeth and to make a replica of the existing teeth.

Since edentulous shapes of patients are very complex, fabrication of dentures requires accurate information including a vertical dimension, a centric relation, a teeth shade, a gum shade, a teeth size and so on. Therefore, it is important to combine and optimize all information required for fabrication of a denture that would fit the patient optimally. Conventional methods incorporate patient information into either a wax or final denture, requiring multiple visits by a patient to a dentist. Moreover, even if a 3D scanner is used, current computer-aided design and computer-aided manufacturing (CAD/CAM) software has a limitation in merging all of the patient's edentulous shape and information.

Generally, designed models may be visualized using a milling machine or 3D printing devices. In particular, 3D printing devices are easy to use and appropriate for fabricating dentures in a relatively short time period.

3D printing technologies, including a selective laser sintering (SLS) method, a fused deposition modeling (FDM) method, a 3D inkjet printing method, a digital light processing (DLP) method, and a stereolithography method, are used in a variety of fields, for example, jewelry, footwear, architecture, engineering and construction, automotive, aerospace, dental and medical industries, education, geographic information systems, civil engineering, and many others. These 3D printing technologies build up layer by layer by adding materials to form 3D objects based on sliced information. The sliced information is generated from a 3D model.

In the fused deposition modeling (FDM) method, the thermoplastics are melted and deposited by an extrusion head, which follows a tool-path defined by a CAD file. The materials are deposited in layers as fine as 25 µm thick, and the part is built from the bottom up, one layer at a time. Some 3D printers based on the fused deposition modeling method are equipped with dual print nozzle heads that can extrude two different materials, one being a building material and the other being a support material. The support material can be washed with water.

3D inkjet printing is effectively optimized for speed, low cost, high resolution, and ease-of-use, making it suitable for visualizing during the conceptual stages of engineering design through to early-stage functional testing. Complicated 3D articles in the ink-jet printing method are produced from photo-curable liquid compositions by jetting followed by UV/Vis light. The photo-curable ink in the ink-jet printing process is jetted through several nozzles on the building platform with a pattern defined by a CAD file.

One of the most efficient technologies among 3D printing technologies is a digital light process (DLP) method or stereolithography (SLA). In a 3D printer using the DLP or SLA method, the photo-curable material, which is in a liquid form, is layered on a vat or spread on a sheet, and a predetermined area or surface of the photo-curable material is exposed to ultraviolet-visible (UV/Vis) light that is controlled by a digital micro-mirror device or rotating mirror. In the DLP method, additional layers are repeatedly or continuously laid and each layer is cured until a desired 3D article is formed. The SLA method is different from the DLP method in that the liquid material is solidified by a line of radiation beam.

In view of the conventional technology for fabricating dentures that require multiple visits by patients to dentists and labor-intensive undertaking, it is desirable to provide a less labor-intensive way of fabricating dentures that requires fewer visits by patients. Further, by employing a 3D scanning and printing technologies, the entire process of preparing dentures may be simplified, shortened, and optimized without sacrificing the quality of the final product.

SUMMARY OF THE INVENTION

The present invention overcomes all of the aforementioned shortcomings by providing a dental apparatus that is convenient to manipulate and software that allows accurate manufacturing of a complete denture without intensive manual labor. Furthermore, the present invention provides method and tools to dentists and patient in order to customize the denture without multiple visit. Therefore, the present invention reduces the number of patient visits, cost and time conventionally required to produce a custom denture.

In accordance with one exemplary embodiment of the present invention, a method for manufacturing a removable dental prosthesis using a dental impression tray assembly, three-dimensional (3D) scanner, 3D design software, and a 3D printer includes: receiving dental impressions of a patient obtained using the dental impression tray assembly during the patient's single visit to a dentist, the dental impressions including a bite registration and at least a mandibular impression or a maxillary impression; receiving information related to the patient's jaw relations obtained using the dental impression tray assembly, the jaw relations including a vertical dimension and a centric relation obtained during the patient's single visit; receiving aesthetic figures including a teeth shade, a gum shade, or a lip length obtained during the patient's single visit; scanning the received dental impressions with the 3D scanner to provide data representative of an edentulous shape of the patient; generating a 3D model of the dental prosthesis by incorporating the received information and aesthetic figures using the 3D design software; displaying the generated 3D model on a display; and 3D printing the dental prosthesis using the 3D printer according to the 3D model.

In accordance with another exemplary embodiment of the present invention, a system for manufacturing a removable dental prosthesis includes: a three-dimensional (3D) scanner configured to scan a bite registration and at least a mandibular impression or a maxillary impression of a patient taken with a dental impression tray assembly to provide data representative of an edentulous shape of the patient; a controller configured to: receive the data from the 3D scanner; receive information related to the patient's jaw relations obtained using the dental impression tray assembly, the jaw relations including a vertical dimension and a centric relation; and generate a 3D model of the dental prosthesis based on the data received from the 3D scanner and the received information related to the patient's jaw relations; a display configured to display the generated 3D model and an application executed for customizing the 3D model; and a 3D printer configured to 3D print the dental prosthesis according to the 3D model.

These and other embodiments will also become readily apparent to those skilled in the art from the following detailed description of the embodiments having reference to the attached figures, the invention not being limited to any particular embodiment disclose.

BRIEF DESCRIPTION OF THE DRAWINGS

The above and other aspects, features, and advantages of the present invention will become more apparent upon consideration of the following description of preferred embodiments, taken in conjunction with the accompanying drawings.

DETAILED DESCRIPTION OF PREFERRED EMBODIMENTS

In the following detailed description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention. Wherever possible, the same reference numbers will be used throughout the drawings to refer to the same or similar parts.

Figure 1:
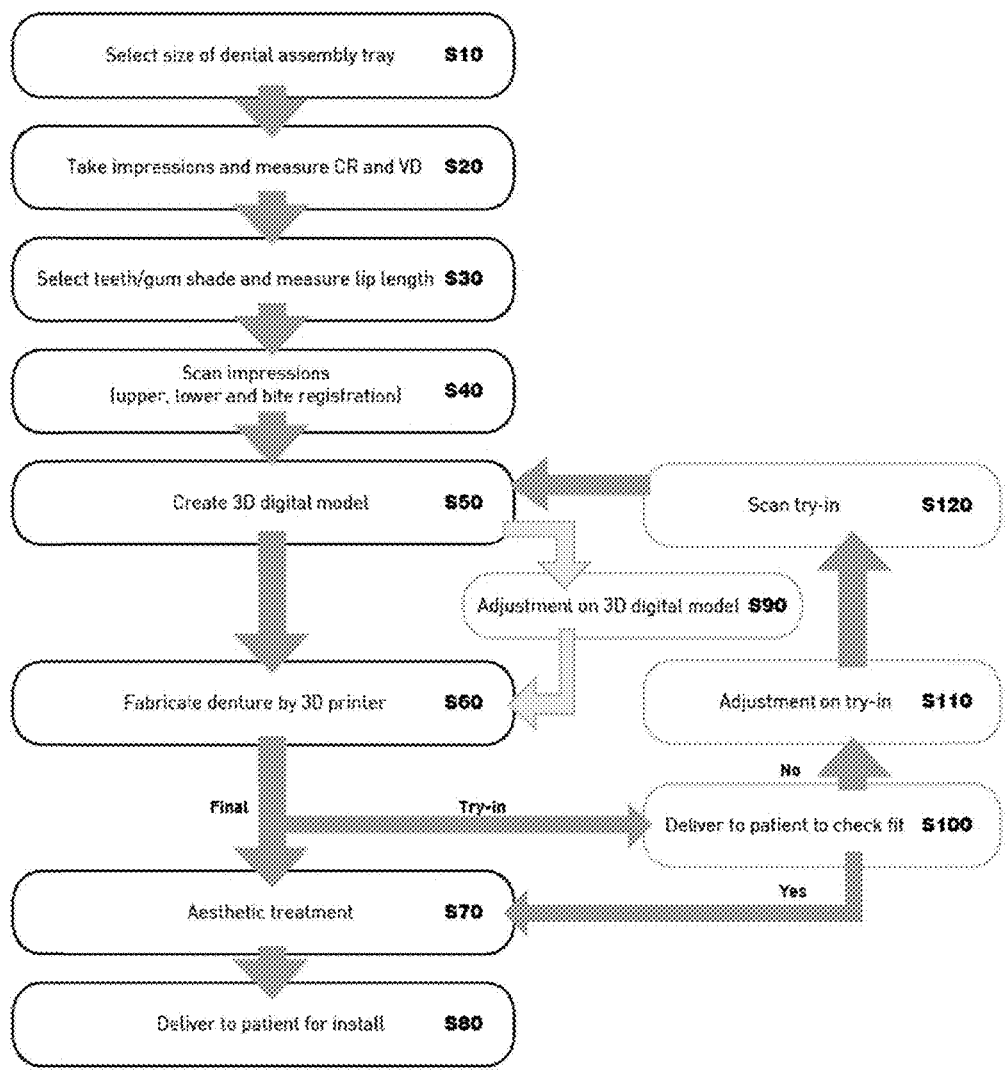
FIG. 1 is a flowchart describing a method for fabricating a removable dental prosthesis according to an embodiment of the present invention.

According to an embodiment of the present invention, an impression of a patient's mouth is taken on a first visit by the patient using a dental tray system and a final denture, or optionally a try-in denture, is manufactured from the impression by using 3D denture fabricating software. Thus, the final denture can be delivered to the patient on the patient's second visit, requiring only two visits by the patient to obtain the final denture. Referring to FIG. 1, the overall process for fabricating a denture is described as follows.

First, on a first visit by a patient, a properly sized dental tray is selected to fit the size of the patient's mouth from a plurality of sizes of dental trays available (S10). Using the selected dental tray, an impression is taken and centric region (CR), vertical dimension (VD), and bite registration are measured (S20). On the same visit by the patient, a teeth shade and a gum shade to be applied to a denture are selected and a lip length of the patient is measured (S30). Thereafter, the impression obtained using the dental tray is scanned by a 3D scanner reflecting the measured bite registration (S40). Then, using 3D design software, a 3D digital model is created based on the vertical dimension and centric relation obtained (S50). The selected teeth shade and gum shade are also applied to the 3D digital model to visualize a denture to be fabricated. The inventive 3D design software allows synthesizing all patient's information to generate the 3D virtual model in a short period of time. The 3D virtual model can be checked and modified on a display by dentists or technicians using the inventive 3D application software (S90). Information about the final 3D digital model is sent to a 3D printer and a denture is fabricated by the 3D printer (S60). At this point, a high quality final denture may be fabricated, applying aesthetic treatment to the final denture (S70) and the final denture is delivered to the patient (S80). Alternatively, prior to fabrication of the final denture, a try-in denture may be generated to confirm proper fitting in the patient's mouth (S100) before delivering the final denture to the patient. If necessary, the try-in denture may be adjusted to better fit the patient's mouth (S110) and the try-in denture is scanned (S120) prior to repeating the process of creating a 3D digital model (S50) and fabricating a denture by the 3D printer (S60) to eventually deliver a final denture to the patient.

Figure 2:
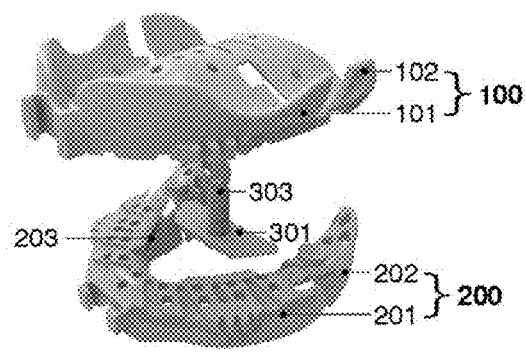
FIG. 2 is a perspective view of a dental tray including several parts that can be assembled/disassembled according to an embodiment of the present invention.
Figure 3:
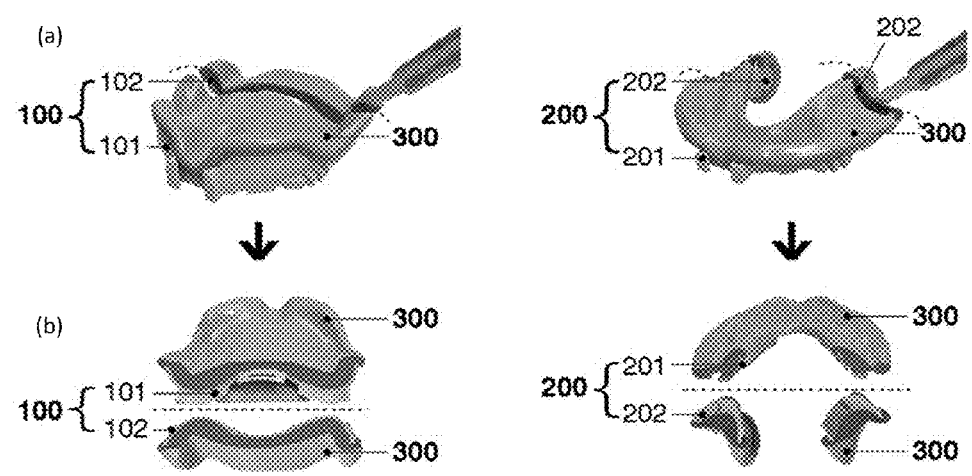
FIG. 3 is a perspective view of an assembled upper tray, a disassembled upper tray, an assembled lower tray, and a disassembled lower tray, each tray with an impression material loaded thereon according to an embodiment of the present invention.

According to an embodiment of the present invention, the inventive set of dental trays used to take the impression includes an upper (maxillary) tray 100 and a lower (mandibular) tray 200, as shown in FIG. 2. The set may also include a uni attachment tray (not shown in drawings) to be used with the upper tray 100 or the lower tray 200 to capture a vertical dimension, a centric relation, and a bite registration if a maxillary or mandibular single arch denture is to be made. The dental trays allow measuring jaw relations and taking a final impression in a single visit by a patient. The set of trays 100 and 200 may be made of plastic or any other suitable material and may be available in various sizes to accommodate different sizes of jaws. The set of trays 100 and 200 may include a plurality of pieces that can be assembled or disassembled. The upper tray 100 includes two pieces 101 and 102, and the lower tray 200 includes a plurality of pieces 201 and 202 as shown in FIGS. 2-3.

The upper tray 100 and the lower tray 200 are used individually to take a maxillary (upper) impression and a mandibular (lower) impression, respectively. When the maxillary impression is taken using the upper tray 100, the upper tray 100, including both the first piece 101 and the second piece 102, as shown in FIG. 3, is inserted into the patient's mouth. Further, when the mandibular impression is taken using the lower tray 200, the lower tray 200, including both the third piece 201 and the pair of fourth pieces 202, as shown in FIG. 3, is inserted into the patient's mouth. For example, as shown in FIG. 3, a polymer material 300, such as polyvinyl siloxane (PVS), is loaded on the first piece 101 and the second piece 102 of the upper tray 100, and the upper tray 100 retaining the polymer material 300 is inserted into the mouth to obtain the maxillary impression of a patient's gum. Specifically, the polymer material 300 is loaded on an upper surface of the upper tray 100. Similarly, as shown in FIG. 3, the polymer material 300 is loaded on the third piece 201 and the pair of fourth pieces 202 of the lower tray 200, and the lower tray 200 retaining the polymer material on its lower surface is inserted into the mouth to obtain the mandibular impression of the patient's gum.

While the polymer material 300 is still on the upper tray 100, as shown in FIG. 3(a), the polymer material 300 is cut, substantially along a single line or borderline (dotted line in FIG. 3(a)) where the first piece 101 and second piece 102 meet. For example, a surgical blade may be used to cut the polymer material 300 on the upper tray 100. Once the polymer material 300 on the upper tray 100 is cut completely, the first piece 101 and the second piece 102 containing the respective cut polymer material are separated carefully, as shown in FIG. 3(b). Excess impression (polymer) material 300 covering outer surfaces of the first piece 101 and the second piece 102 may be trimmed so that bite registration material can be seated. Similarly, the polymer material 300 on the lower tray 200 is cut substantially along a single line between the third piece 201 and the pair of fourth pieces 202, as shown in FIG. 3(a). Once the polymer material 300 on the lower tray 200 is cut completely, the pair of fourth pieces 202 are carefully separated from the third piece 201, as shown in FIG. 3(b).

Thereafter, the first piece 101 and the third piece 201 retaining the partial impression (polymer material 300), as shown in FIG. 3(b), are inserted into the mouth together with an intra-oral tracer 301 attached to the third piece 201 (shown in FIG. 2). The intra-oral tracer 301 is shaped to receive a pin 303 at a substantially central area of the intra-oral tracer 301, as shown in FIG. 2. For example, the pin 303 may be formed as a screw and the screw is inserted into a screw hole formed at the substantially central area or at a middle portion of the intra-oral tracer 301 such that the pin 303 can be raised or lowered by rotating the pin 303 through the screw hole. Preferably, the pin 303 has at least one tip having a pointed end. More preferably, the tip of the pin 303 directed upward toward the first piece 101 has a pointed end.

The intra-oral tracer 301 is inserted into a receiving portion 203 of the third piece 201 of the lower tray 200, as shown in FIG. 2, to be inserted into the mouth. For example, the receiving portion 203 is formed at a side that is opposite to a side of the third piece 201 retaining the impression (polymer material 300). The receiving portion 203 of the third piece 201 may be formed as a slot at an upper inner surface of the third piece 201 such that edge portions of the intra-oral tracer 301 are inserted to the slot. In one embodiment, two slots are formed at an upper inner side surface of the third piece 201, the two slots facing each other such that one side edge of the intra-oral tracer 301 is inserted into one slot and the other side edge of the intra-oral tracer 301 is inserted into the other slot.

Figure 4:
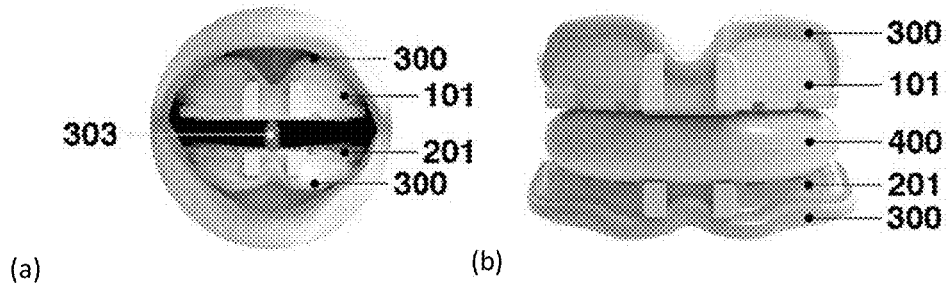
FIG. 4 is a perspective view of a centric relations record and bite registration material using a disassembled lower and upper trays with an bite registration material loaded.

A tracing material is applied to the first piece 101 of the upper tray 100 such that the pin 303 of the intra-oral tracer 301 contacts the applied tracing material when the first piece 101 and the third piece 201 are inserted into the mouth together with the intra-oral tracer 301 attached to the third piece 201 to measure jaw relations such as a vertical dimension (VD) and a centric relation (CR). When the upper tray 100 and the lower tray 200 are inserted into the mouth together, the second piece 102 and the pair of fourth pieces 202 are not attached to the first piece 101 and the third piece 201, respectively, because both the first piece 101 and the third piece 201 are sized to be placed together in a patient's mouth without the second piece 102 and the pair of fourth pieces 202. Further, if the pin 303 of the intra-oral tracer 301 has a tip with the pointed end, the tip with the pointed end is directed upward to contact the tracing material applied to the first piece 101 in the mouth as shown in FIG. 4(a). The tracing material is not shown in the drawings.

Jaw relations are measured by lowering or raising the pin 303 of the intra-oral tracer 301 that is in contact with the first piece 101 in the mouth until patient's lips naturally touch each other without the lips having any tension. Once the intra-oral tracer 301 is adjusted to be in a clinically acceptable position, the vertical dimension is measured and the centric relation is determined by having the patient move his/her jaw front and back several times to capture the most posterior position. In case when the patient already has a denture, a vertical dimension is determined by adjusting the pin 303 to match a predetermined vertical dimension. When the first piece 101 and the third piece 201 are in the mouth to determine the centric relation, the pointed end of the pin 303 is directed upward, thus contacting the tracing material applied to the first piece 101. Therefore, when the patient's jaw is moved, the centric relation is traced according to movement of the pin 303.

After determining the centric relation position, a polymer material 400, such as PVS, is filled in a gap between the first piece 101 and the third piece 201 to obtain a bite registration as shown in FIG. 4(b). After the polymer material 400 is filled to obtain the bite registration, the entire piece, including the first piece 101 and the third piece 201, is removed from the patient's mouth. Further, a length of the patient's lip is measured from incisive papilla to an upper lip line, using a lip ruler.

In order to measure the jaw relation record and record the centric relation, the mouth of the patient needs to be able to accommodate the trays when they are inserted into the mouth. However, if full-sized trays, such as conventional trays, are inserted into the mouth, it is difficult for the patient's mouth to accommodate the full-sized conventional trays because the end portions of the upper and lower trays contact each other at the posterior position of the mouth, thus becoming very bulky in the mouth. In order to solve this problem, the trays of the present invention have been sized to be accommodated in the mouth. For example, the first piece 101 of the upper tray 100 and the third piece of the lower tray 200 cover at least an anterior position of the mouth while not covering the entire region of the mouth. Therefore, according to the present example, jaw relations can be measured after obtaining the full impression of the patient's gum first using the full-sized upper tray 100 and the lower tray 200 individually, and then by cutting the obtained impression and separating the first piece 101 and the second piece 102 of the upper tray 100 and separating the third piece 201 and the pair of fourth pieces 202 of the lower tray 200.

The shapes of the trays have unique dimensions, the first piece 101 providing the position of the tray and the third piece 201 supporting the borders and capturing muscle movements. The first and third pieces 101 and 201 may have openings to retain the impression material.

Figure 5:
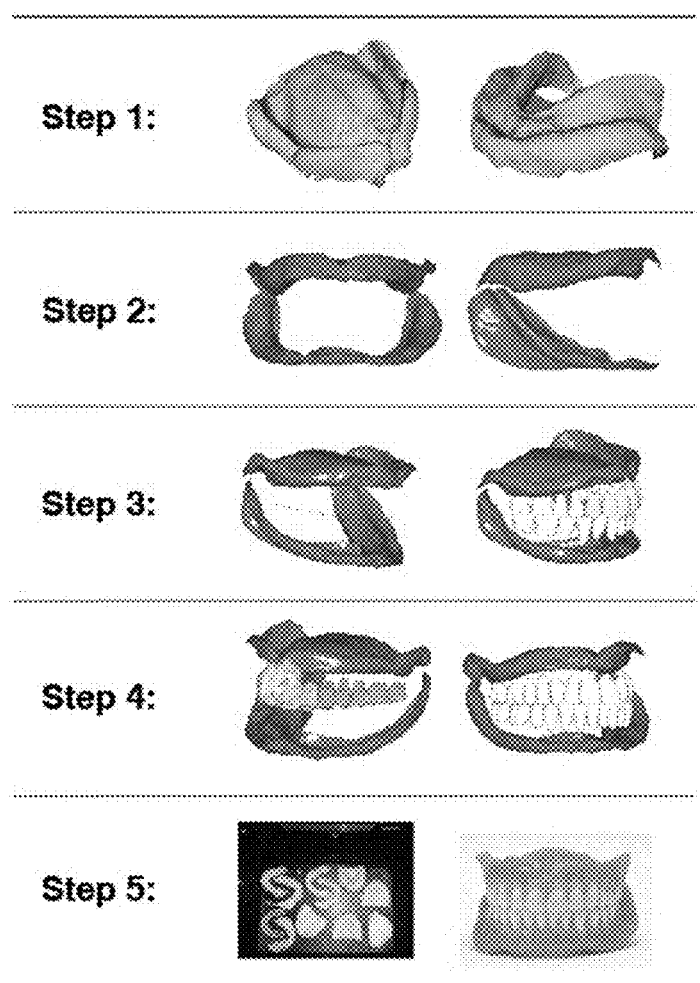
FIG. 5 is a flowchart describing steps for generating a 3D virtual model using design software based on information obtained from a patient during the patient's single visit according to an embodiment of the present invention.

After the patient's oral tissue shape, centric relation, and bite registration are obtained, and the gum shade, teeth shade are selected during the patient's first visit, the maxillary impression, mandibular impression, and bite registration are scanned by a 3D scanner to generate a 3D model in a computer. Step 1 in FIG. 5 shows the scanned data after receiving all of the patient's information for the digital design. According to an embodiment of the present invention, software is used to obtain a virtual model of the denture to be fabricated from the scanned data. Since the bite registration has been taken between the dental trays 101, 201, the digital maxillary and mandibular impressions can be located digitally based on the bite registration and articulated using the inventive software as shown in step 2 of FIG. 5. Furthermore, the information on the vertical dimension and centric relation obtained using the inventive tray assembly is input into the software to create the denture. The inventive design software is used to fabricate a denture by taking the measurements of edentulous regions of the maxilla and mandible from the respective impressions.

In step 3 of FIG. 5, the design software synthesizes all the data and creates a 3-D model of the edentulous ridge and borders, forms a 3D postdam in the 3D model, and generates placement of the teeth and gingival tissue in the 3D model. One of retention elements of a maxillary complete denture is a complete border seal in order to achieve suction. The border seal is composed of the edges of anterior and lateral areas and the posterior palatal seal. Proper design of a postdam contacting the posterior palatal seal is one of important factors to accomplish the suction and it must cover the entire hard palate and should not extend beyond the soft palate and end at 1-2 mm from a vibrating line. When a well-designed postdam is completed, the peripheral seal is achieved, thus bringing stability of the maxillary denture. Included in the software are various sets of teeth types, varying based on a shape, a size and a color. After selecting a desired tooth type, the software generates a virtual denture with the above-identified reference points to correctly place the teeth with respect to the denture. Furthermore, the software corrects any overlap of tooth structure that may arise from a discrepancy between the selected tooth type and the measurements entered from the impressions and gathered data. Once the virtual denture is created, it is colored based on the selected teeth and gum shades to provide a natural look. In step 4 of FIG. 5, the modeler revises and finalizes the denture model and makes additional adjustments if requested by the dentist.

Figure 6:
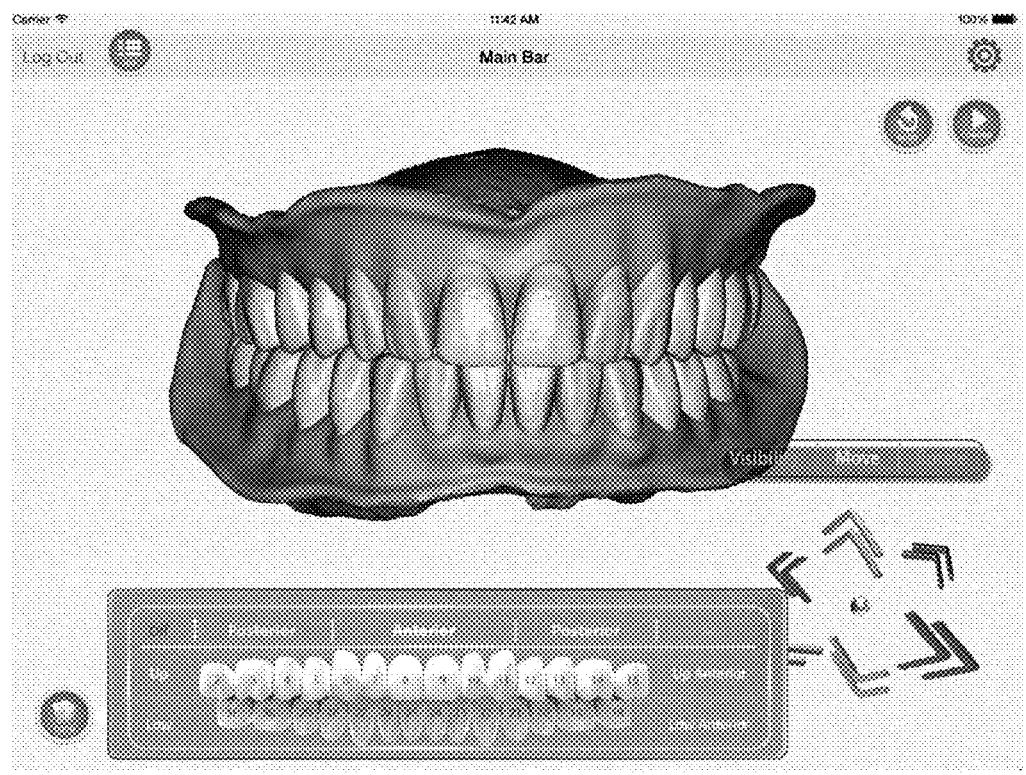
FIG. 6 shows a screenshot of executed application software allowing modification of a teeth set-up using the application software according to an embodiment of the present invention.

According to an embodiment of the present invention, the 3D model denture can be checked and modified by dentists according to the patient's preference in two different ways. A first method is performing digital check-up on the digital 3D denture model using the inventive application software. The designed 3D denture file is delivered to dentists such that dentists may check and revise teeth set-up using the inventive application software. FIG. 6 shows an example of an application of inventive application software displayed on a display allowing dentists to modify the teeth set-up. The dentists can see the denture in 3D space and may realign and modify the teeth set-up on the display using the application software if necessary.

A second method is performing physical check-up using the 3D printed try-in. Optionally, dentists can receive the try-in denture before final denture is manufactured. If an adjustment or corrections need to be made, dentists can make desired changes to generate an individually customized denture. An advantage of these methods is that dentists and patients are able to see the 3D denture model and modify the same according to their preference. Therefore, the system is capable of providing completed dentures in a relatively short period of time compared to the conventional way of manufacturing dentures. In addition, the inventive methods can save the dentist's working progress time and also improve patient satisfaction.

Figure 7:
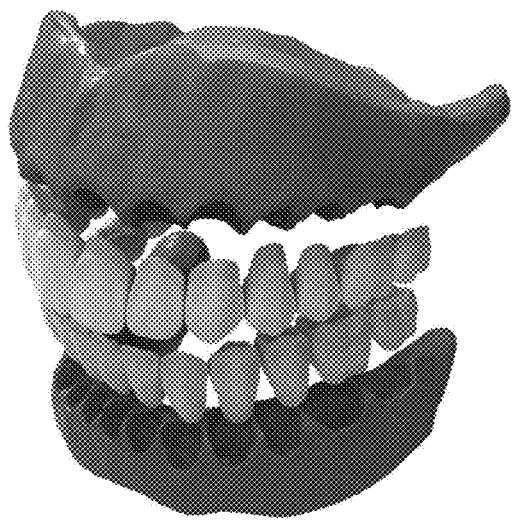
FIG. 7 shows a 3D model generated according to information obtained using the dental tray according to an embodiment of the present invention.

In step 5 of FIG. 5, an electronic file of the generated and finalized 3D model is transferred to a 3D printer to allow fabrication of a custom denture. FIG. 7 shows an example of a 3D model of a denture in which a teeth portion and a gingival portion are separated. According to the 3D printing method, the denture base and teeth can be printed separately or as an one body using a different material and colors.

There are various types of 3D printers available. For example, a 3D printing system using a fused deposition modeling (FDM) method, an ink-jet printing method, a digital light processing (DLP) method, or stereolithography method (SLA) may be used for fabricating dentures. The FDM method uses thermoplastic materials that can be extruded through tiny nozzles by melting the materials. In order to generate a multi-colored denture, an FDM printer uses several cartridges to extrude various colors. An ink-jet printer, DLP type printer, and SLA type printer use photocurable compositions that can be colored with pigments. For example, the photo-curable compositions may be light-curable viscous mixtures including a polymethyl methacrylate/methyl methacrylate mixture, difunctional bisphenol A dimethacrylate, multifunctional methacrylate, urethane dimethacrylate, surface modified silica-based fine particles, a light-photo-polymerization initiator, a colorant, and at least one type of stabilizer.

For ink-jet printer, these colored materials injected through a series of tiny nozzles of the ink-jet printer are exposed to UV/Vis light in order to be solidified. A DLP printer may be used to generate dentures by separately printing a denture base and artificial teeth that are glued together using dental adhesives. A SLA printer uses the similar building method such as DLP but the SLA method uses a line of beam to generate one layer instead of projected one layer in DLP method. All of these 3D printers generate dentures using a layer-by-layer build-up method. Once a denture is printed using a 3D printer, the denture is delivered to a patient for trial.

Various embodiments described herein may be implemented in a computer-readable medium, a machine-readable medium, or similar medium using, for example, software, hardware, or any combination thereof. For a hardware implementation, the embodiments described herein may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a selective combination thereof.

For a software implementation, certain embodiments described herein may be implemented with separate software modules, such as procedures and functions, each of which perform one or more of the functions and operations described herein. The software codes can be implemented with a software application written in any suitable programming language and may be stored in memory, and executed by a controller or processor.

According to yet another embodiment of the present invention, the final denture is milled based on the above described information. Upon receiving the file of the virtual denture generated by the software, a machine will mill an acrylic block into the real denture. The milling denture comprises two different pieces. The first piece is on the teeth portion, and the second piece is on the gingival portion. Each piece is milled separately, and after milling, the two pieces are put together to form the denture.

Alternatively, the denture may be fabricated by rapid prototyping or a combination of the rapid prototyping and a conventional flasking technique. This allows different colors to be used to represent gingival and teeth colors in one operation, using the colors from the rapid prototyping, which are derived from the model.

The present disclosure relates to the art and science of dental prosthetics whereby dental professionals can produce a high quality complete denture at a substantially reduced cost, and in a reduced time, by using newly invented devices and software. It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A method for manufacturing a removable dental prosthesis using a dental impression tray assembly, three-dimensional (3D) scanner, 3D design software, and a 3D printer, the method comprising:
   receiving dental impressions of a patient obtained using the dental impression tray assembly, the dental impressions including a bite registration and at least a mandibular impression or a maxillary impression;
   receiving information related to the patient's jaw relations obtained using the dental impression tray assembly, the jaw relations including a vertical dimension and a centric relation;
   receiving aesthetic figures including a teeth shade, a gum shade, or a lip length;
   scanning the received dental impressions with the 3D scanner to provide data representative of an edentulous shape of the patient;
   generating a 3D model of the dental prosthesis by incorporating the received information using the 3D design software;
   displaying the generated 3D model on a display; and
   3D printing the dental prosthesis using the 3D printer according to the 3D model,
   wherein the dental impression tray assembly comprises:
      an upper tray configured to receive impression material for taking a first impression of the patient's gum and sized to be inserted into the patient's mouth; and
      a lower tray comprising:
         a first piece configured to receive impression material for taking a second impression of the patient's gum and sized to be inserted into the patient's mouth, wherein the first piece is curved at about a central portion to form a right end portion and a left end portion; and
         a pair of second pieces detachably coupled to the first piece, a right piece of the pair of second pieces coupled to the right end portion of the first piece and a left piece of the pair of second pieces coupled to the left end portion of the first piece.

2. The method of claim 1, wherein the aesthetic figures further include at least a teeth size or midline that are incorporated into the 3D model.

3. The method of claim 1, further comprising incorporating at least one of edentulous borders, a teeth set-up, or retention elements into the 3D model using the 3D design software.

4. The method of claim 1, further comprising providing application software executable on a computer to at least the dentist or the patient, allowing at least the dentist or the patient to modify or adjust the 3D model using the application software.

5. The method of claim 1, further comprising separating a gum portion and a teeth portion of the 3D model, and 3D printing the gum portion and the teeth portion separately.

6. The method of claim 1, further comprising 3D printing the dental prosthesis by a ink-jet printing method, a digital light processing method, or a sterolithography method in which photo-curable compositions for the dental prosthesis are used.

7. The method of claim 6, wherein the photo-curable compositions comprise at least one of mono and multifunctional methacrylates, aliphatic urethane methacrylates, silica powder, poly(methyl methacrylate) beads, photo-initiator, stabilizer, or pigment.

8. The method of claim 6, wherein the photo-curable compositions comprise light-curable viscous mixtures comprising a poly(methyl methacrylate)/methyl methacrylate mixture, difunctional bisphenol A dimethacrylate, multifunctional methacrylate, urethane dimethacrylate, surface modified silica-based fine particles, a light-photo-polymerization initiator, a colorant, and at least one type of stabilizer.

9. The method of claim 1, wherein:
   the dental impression, the vertical dimension, the centric relation, the teeth shade, the gum shade, and the lip length are obtained during the patient's single visit to a dentist or dental professional; and
   the aesthetic figures are incorporated into the 3D-printed dental prosthesis.

10. The method of claim 1, wherein the upper tray comprises:
    a third piece configured to measure the jaw relations of the patient's mouth along with the first piece of the lower tray,
    wherein the third piece is sized to cover the patient's upper anterior gum and has a front portion and a rear portion.

11. The method of claim 10, wherein:
    the upper tray further comprises a fourth piece configured to be detachably coupled to the rear portion of the third piece;
    the first impression is taken by inserting the third piece into the patient's mouth with the fourth piece attached;
    the fourth piece is detached from the third piece after the first impression is obtained; and
    the third piece retaining the first impression and the first piece of the lower tray retaining the second impression are inserted together into the mouth to determine the jaw relations.

12. The method of claim 11, wherein the fourth piece of the upper tray is sized to cover a distal portion or a remaining portion of the patient's upper gum when attached to the third piece.

13. The method of claim 1, wherein:
    the dental impression tray assembly further comprises an intra-oral tracer that is configured to be detachably coupled to the first piece of the lower tray; and
    the intra-oral tracer is inserted into the mouth to be placed between the upper tray and the first piece of the lower tray and to measure a vertical dimension and a centric relation.

14. The method of claim 13, wherein:
    the dental impression tray assembly further comprises a dental tracing apparatus comprising three layers, one of the three layers being removed to expose an adhesive surface of another one of the three layers such that the dental tracing apparatus is attached to a surface of the upper tray via the adhesive surface; and
    the centric relation is recorded using the dental tracing apparatus.

15. The method of claim 14, wherein:
    the intra-oral tracer comprises an adjusting member that is inserted through an adjusting member receiving portion formed at a middle portion of the intra-oral tracer;

the centric relation is recorded on the dental tracing apparatus according to movement of the adjusting member that is in contact with the dental tracing apparatus in the patient's mouth; and the adjusting member is raised or lowered to determine the vertical dimension and to adjust a size of the gap for receiving the bite registration material.

16. A system for manufacturing a removable dental prosthesis, the system comprising:

a three-dimensional (3D) scanner configured to scan dental impressions including a bite registration and at least a mandibular impression or a maxillary impression of a patient taken with a dental impression tray assembly to provide data representative of an edentulous shape of the patient;

a controller configured to:
 receive the data from the 3D scanner;
 receive information related to the patient's jaw relations obtained using the dental impression tray assembly, the jaw relations including a vertical dimension and a centric relation;
 receive aesthetic figures including a teeth shade, a gum shade, or a lip length; and
 generate a 3D model of the dental prosthesis based on the data received from the 3D scanner and the received information using 3D design software;

a display configured to display the generated 3D model and an application executed for customizing the 3D model; and a 3D printer configured to 3D print the dental prosthesis according to the 3D model, wherein the dental impression tray assembly comprises:
 an upper tray configured to receive impression material for taking a first impression of the patient's gum and sized to be inserted into the patient's mouth; and
 a lower tray comprising:
  a first piece configured to receive impression material for taking a second impression of the patient's gum and sized to be inserted into the patient's mouth, wherein the first piece is curved at about a central portion to form a right end portion and a left end portion; and
  a pair of second pieces detachably coupled to the first piece, a right piece of the pair of second pieces coupled to the right end portion of the first piece and a left piece of the pair of second pieces coupled to the left end portion of the first piece.

17. The system of claim 16, wherein the 3D printer is further configured to 3D print the dental prosthesis by a ink-jet printing method, a digital light processing method, or a stereolithography method in which photo-curable compositions are used.

18. The system of claim 17, wherein the photo-curable compositions comprise at least one of mono and multifunctional methacrylates, aliphatic urethane methacrylates, silica powder, poly(methyl methacrylate) beads, photo-initiator, stabilizer, or pigment.

19. The system of claim 17, wherein the photo-curable compositions comprise light-curable viscous mixtures comprising difunctional bisphenol A dimethacrylate, multifunctional methacrylate, urethane dimethacrylate, surface modified silica-based fine particles, a light-photo-polymerization initiator, a colorant, and at least one type of stabilizer.

20. The system of claim 16, wherein the dental impression tray assembly further comprises:

an intra-oral tracer that is configured to be detachably coupled to the first piece of the lower tray, the intra-oral tracer comprising an edge portion that is inserted into a receiving portion of the first piece.

21. The system of claim 16, wherein:

the controller is further configured to separate a gum portion and a teeth portion of the 3D model; and the 3D printer is further configured to 3D print the gum portion and the teeth portion separately.

* * * * *